United States Patent [19]

O'Neill

[11] 4,258,725
[45] Mar. 31, 1981

[54] PACING LEAD WITH STYLET AND TAPERED TERMINAL PIN

[75] Inventor: Edward G. O'Neill, St. Paul, Minn.

[73] Assignee: Medtronic, Inc., Minneapolis, Minn.

[21] Appl. No.: 77,868

[22] Filed: Sep. 21, 1979

[51] Int. Cl.³ .............................................. A61N 1/00
[52] U.S. Cl. ................................................. 128/419 P
[58] Field of Search .................... 128/419 P, 784–786

[56] References Cited

U.S. PATENT DOCUMENTS

| 3,437,091 | 4/1969 | Jerushalmi et al. | 128/786 |
| 4,030,508 | 6/1977 | Thalen | 128/419 P |
| 4,106,512 | 8/1978 | Bisping | 128/419 P |

Primary Examiner—William E. Kamm
Attorney, Agent, or Firm—John L. Rooney; Joseph F. Breimayer; Lew Schwartz

[57] ABSTRACT

Terminal pin which engages into a wire coil of a transvenous pacing lead and mechanically attaches to the wire coil with a metal crimping sleeve which engages over the wire coil. The terminal pin includes a tapered distal end portion from an outward radial shoulder in a midportion of the terminal pin to the distal end of the terminal pin. A stylet easily passes through a longitudinal hole extending through the terminal pin and into the wire coil of the transvenous pacing lead.

5 Claims, 1 Drawing Figure

PACING LEAD WITH STYLET AND TAPERED TERMINAL PIN

BACKGROUND OF THE INVENTION

1. Field of the Invention

The present invention relates generally to a terminal pin, and more particularly, pertains to a terminal pin for use with a transvenous pacing lead for connection to a cardiac pulse generator.

2. Description of the Prior Art

Prior art terminal pins in transvenous pacing leads have usually presented particular problems during manufacture of the pacing lead and subsequent passage of a stylet through the terminal pin in the transvenous pacing lead. In the past, terminal pins have usually required a crimping sleeve inside the wire coil of the transvenous pacing lead which usually presented particular difficulty in attachment during manufacturing of the terminal pin to the coil forming the transvenous pacing lead with the terminal pin affixed to one end of the coil.

In the prior art practice, a sleeve was positioned on the inside of the coil and a terminal pin on the outside of the coil, and subsequently crimped about the coil and crimping sleeve which required precise positioning of the crimping sleeve and the terminal pin. As a consequence, manufacturing was a particular complex precise assemblage. Passage of the stylet through the terminal pin at the sleeve was also a problem as the stylet would tend to hang up or catch on the sleeve or wire coil requiring a number of stabs for passage of the stylet tip past the junction of the terminal pin sleeve and wire coil at the proximal end of the transvenous pacing lead. The stabbing and manipulating of the stylet wire is also frustrating to medical personnel.

The present invention overcomes the disadvantages of the prior art by providing a terminal pin having an angular tapered member which easily fits into the wire coil of the transvenous pacing lead.

SUMMARY OF THE INVENTION

The general purpose of the present invention is to provide a terminal pin which easily fits into a wire coil of a transvenous pacing lead, and easily accepts passage of a stylet through the terminal pin.

According to one embodiment of the present invention, there is provided a terminal pin including a member having a longitudinal hole running therethrough, an outwardly extending shoulder about a midportion of the member, a distal end of the member tapered downwardly in a conical configuration from a large diameter at the shoulder to a small diameter at the distal tip, and a proximal portion of the member having a constant diameter whereby the distal end of the member engages into a wire coil of a transvenous pacing lead and the wire coil is subsequently crimped between the tapered proximal end of the member of the terminal pin and a crimping sleeve engaged between the distal end of the member and the wire coil.

A significant aspect and feature of the present invention is a terminal pin which functionally engages into the wire coil of the transvenous pacing lead. This provides for easy passage of a stylet through the terminal pin and through the wire coil of the pacing lead, and prevents the catching of the stylet on the terminal pin. Easy passage of the stylet through the terminal pin is extremely important and the present invention overcomes the problems of the prior art in providing for the easy passage of a stylet.

Another significant aspect and feature of the present invention is ease of manufacture of the proximal end of a transvenous pacing lead including the terminal pin mating to the wire coil of the pacing lead.

BRIEF DESCRIPTION OF THE DRAWINGS

Other objects and many of the attendant advantages of this invention will be readily appreciated as the same becomes better understood by reference to the following detailed description when considered in connection with the accompanying drawing in which like reference numerals designate like parts throughout the FIGURE thereof and wherein.

DETAILED DESCRIPTION OF A PREFERRED EMBODIMENT

Figure 1:
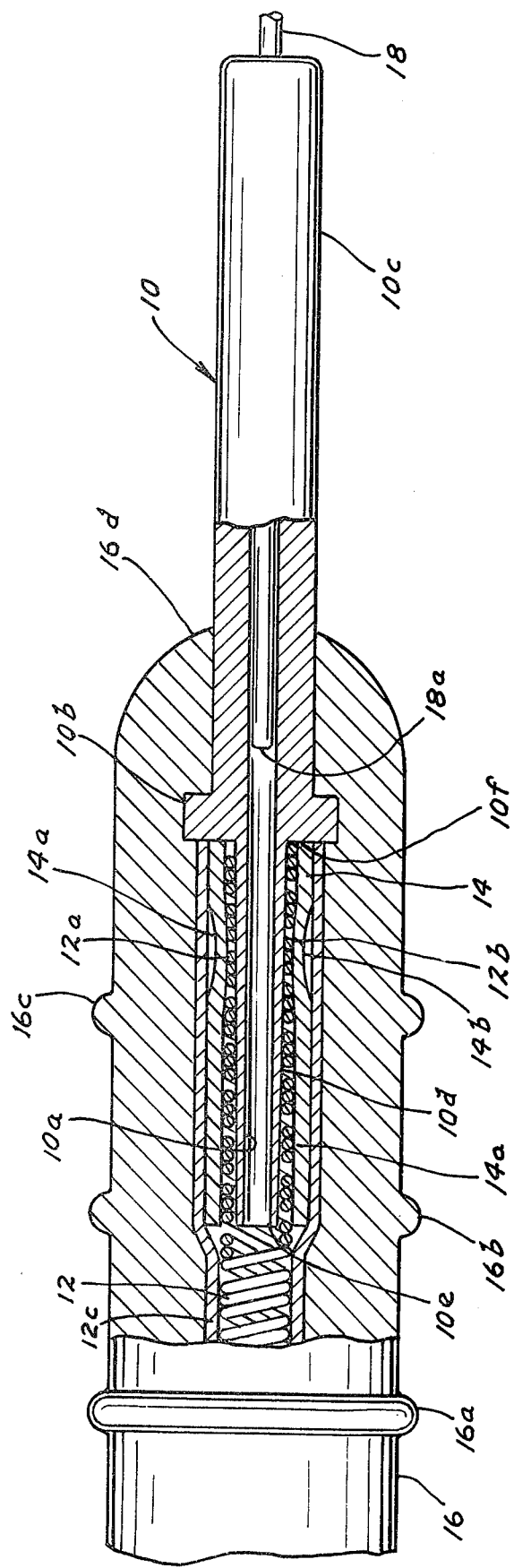
FIG. 1 illustrates a plan view of a terminal pin, the present invention, partly in cross-section in a transvenous pacing lead.

FIG. 1, which illustrates a plan view of a terminal pin 10, the present invention, partly in cross-section, shows the terminal pin 10 including a longitudinal hole 10a running the longitudinal length of a member of terminal pin 10, a circumferential radially projecting shoulder 10b in a midportion of the terminal pin 10, a proximal end portion 10c extending outwardly towards the end of the terminal pin 10 and having a constant diameter, and a distal end portion 10d extending from the shoulder 10b to the distal tip 10e of the terminal pin 10. The distal portion 10d angularly decreases from the shoulder 10b to the distal tip 10e such that the outer diameter is always decreasing and providing a taper from the shoulder 10b to the distal tip 10e. An outer diameter 10f of the distal portion 10d of the shoulder 10b is slightly larger than the inner diameter of a wire coil, such as a trifilar space-wound coil by way of example and for purposes of illustration only, of a transvenous pacing lead and the outer diameter of the distal tip 10e is substantially equal to the inner diameter of the wire coil 12. An outer metal sleeve 14 including an inner diameter slightly larger than the outer diameter of the coil 12 engages over the outer diameter of the coil 12 and is mechanically crimped at a plurality of points, 14a and 14b, being illustrated, resulting in mechanical attachment of the wire coil 12 at adjacent points 12a and 12b between the distal portion 10d of the terminal pin 10 and crimps 14a and 14b of the outer sleeve 14. Other perpendicularly opposed crimps are not illustrated in the FIGURE for purposes of clarity of illustration in the FIGURE. Urethane or like insulation material 12c covers the wire coil 12, extends over the metal sleeve 14, and abuts up against the shoulder 10b of the terminal pin 10. A connector sleeve 16 of silicone rubber or like material extends over the insulation 12c of the wire coil 12, the shoulder 10b, and a portion of the proximal end portion 10c of the terminal pin 10 terminating at a rounded portion 16d and including circumferential sealing rings 16a, 16b, and 16c.

PREFERRED MODE OF OPERATION

The terminal pin 10 is utilized in a conventional way in that the outer metal sleeve 14 is first inserted between the wire coil 12 and the insulation 12c covering the wire coil 12, and subsequently the tapered distal portion 10b of the terminal pin 10 is inserted into the wire coil 12. Subsequently and by any known mechanical tools in the art, the metal sleeve 14 is mechanically crimped or swaged at points 14a and 14b and other points not illustrated in the FIGURE for purposes of clarity causing mechanical engagement of the coil at points 12a and 12b between the distal portion 10b of the terminal pin 10 and points 14a and 14b of the metal sleeve 14.

In use, a stylet 18 having a stylet tip 18a is inserted down through the longitudinal hole 10a of the terminal pin member 10, and subsequently passes unhindered into and through the wire coil 12. The transition from the distal tip 10e of the terminal pin 10 into the wire coil 12 is considered a smooth transition without any voids or other objects providing friction or engagement to the tip 18a of the stylet 18. The stylet 18 passes with ease through the terminal pin 10.

Various modifications can be made to the terminal pin 10 of the present invention without departing from the apparent scope thereof.

Having thus described the invention, what is claimed is:

1. A cardiac pacing lead having a stylet comprising:
   a coiled conductor having a proximal end;
   sheath means of material substantially inert to body fluids covering said coiled conductor;
   a terminal pin having a proximal end, having a longitudinal aperture, and having a distal portion with a distal tip of a smaller outside diameter than the remainder of said distal portion within said proximal end of said coiled conductor, whereby the insertion of said stylet into said longitudinal aperture at said proximal end of said terminal pin and therefrom via said distal portion of said terminal pin into said coiled conductor is facilitated by said smaller outside diameter; and
   outer sleeve means frictionally attached to said proximal end of said conductor coil, whereby said proximal end of said conductor coil is caused to frictionally engage said distal portion of said terminal pin.

2. A cardiac pacing lead according to claim 1 further comprising:
   a shoulder fixedly attached to said terminal pin intermediate said distal portion of said terminal pin and said proximal end of said terminal pin.

3. A cardiac pacing lead according to claim 2 wherein said terminal pin further comprises:
   a proximal portion located intermediate said shoulder and said proximal end of said terminal pin having a cylindrical shape of substantially uniform diameter.

4. A cardiac pacing lead according to claim 3 wherein said distal portion of said terminal pin has a truncated conical shape.

5. A cardiac pacing lead according to claim 4 further comprising:
   a connector sleeve of insulating material substantially inert to body fluids fixedly attached to and covering a portion of said terminal pin.

* * * * *